United States Patent [19]

Shell et al.

[11] Patent Number: 5,186,922
[45] Date of Patent: Feb. 16, 1993

[54] USE OF BIODEGRADABLE MICROSPHERES LABELED WITH IMAGING ENERGY CONSTRAST MATERIALS

[75] Inventors: William E. Shell, Los Angeles; Jackie R. See, Fullerton, both of Calif.

[73] Assignee: See/Shell Biotechnology, Inc., Los Angeles, Calif.

[21] Appl. No.: 462,740

[22] Filed: Jan. 8, 1990

Related U.S. Application Data

[63] Continuation of Ser. No. 937,697, Oct. 4, 1986, abandoned, which is a continuation-in-part of Ser. No. 712,038, Mar. 15, 1985, Pat. No. 4,680,171.

[51] Int. Cl.$^5$ ............................................. A61K 49/04
[52] U.S. Cl. ........................................ 128/654; 424/9; 424/5; 514/5; 128/691
[58] Field of Search ............ 128/653 CA, 645; 660/1, 660/3, 9; 604/20; 424/1.1, 4, 9, 489, 5, 490; 514/5

[56] References Cited

U.S. PATENT DOCUMENTS

| | | | |
|---|---|---|---|
| 3,937,668 | 2/1976 | Zolle | 424/2 X |
| 4,126,669 | 11/1978 | Rothman et al. | 424/9 X |
| 4,680,171 | 7/1987 | Shell | 424/5 |
| 4,709,703 | 12/1987 | Lazarow et al. | 128/654 |
| 4,827,945 | 5/1989 | Groman et al. | 128/653 |
| 4,834,864 | 5/1989 | Rosa | 424/9 |
| 4,849,210 | 7/1989 | Widder | 424/9 |
| 4,863,715 | 9/1989 | Jacobson et al. | 424/9 |
| 4,871,716 | 10/1989 | Longo et al. | 514/2 |
| 5,019,370 | 5/1991 | Jay et al. | 424/4 |
| 5,088,499 | 2/1992 | Unger | 128/662.02 |

FOREIGN PATENT DOCUMENTS 8606605  11/1986  PCT Int'l Appl. .......... 128/653 CA Primary Examiner—John D. Yasko
Assistant Examiner—Mark O. Polutta
Attorney, Agent, or Firm—Robert J. Schaap

[57] ABSTRACT

The invention relates to an inexpensive and easy to use method of visualizing an arterial circulation, using biodegradable microspheres which are permeated with an imaging energy absorbent contrast material, such as an X-ray absorbent material, which enables the diagnosis of pulmonary embolism. The microspheres may be comprised of a variety of materials, including human albumin, and may be dyed with a number of X-ray absorbent materials, or other imaging energy absorbent materials. The microspheres are injected into the bloodstream at a particular location such that they travel through the desired circulation, e.g. an arterial circulation and ultimately become lodged in the capillaries of a tissue of interest. Upon exposure of the arterial circulation to X-rays, blood vessels therein containing the microspheres will absorb the X-rays, causing them to show on a developed X-ray film in contrast to other blood vessels and body tissue which do not contain the microspheres that transmit the X-rays. The microspheres are designed to dissolve into the bloodstream within fifteen to thirty minutes after their introduction, the X-ray dye or other contrast material being ultimately excreted from the body via the urine or metabolized by the liver.

21 Claims, No Drawings

USE OF BIODEGRADABLE MICROSPHERES LABELED WITH IMAGING ENERGY CONSTRAST MATERIALS

RELATED APPLICATION

This application is a continuation of our co-pending patent application Ser. No. 937,697, filed Oct. 4, 1986, now abandoned, for "Use of Biodegradable Microspheres Labelled With Imaging Energy Contrast Materials", which is, in turn, is a continuation-in-part of our co-pending patent application Ser. No. 712,038, filed Mar. 15, 1985 now U.S. Pat. No. 4,680,171 for "Use of Biodegradable Microspheres Dyed With X-ray Opaque Material To Visualize An Arterial Circulation, Enabling The Diagnosis of Pulmonary Embolism".

BACKGROUND OF THE INVENTION

1. Field of the Invention

This invention relates generally to the visualization of an arterial circulation, including e.g. diagnosis of pulmonary embolism and, more particularly, to the visualization of an arterial circulation of using biodegradable microspheres laden with a contrast material, such as an X-ray absorbent or opaque material.

2. Brief Description of the Prior Art

Decreased blood flow to various organs is a danger faced by all mammals, particularly man. A decrease in blood flow to the lungs is especially dangerous, since it is in the lungs that oxygen is incorporated into the blood for distribution throughout the body.

A blood clot in the lungs, which is one cause of decreased blood flow, gives rise to a disease known as pulmonary embolism. This is one of the most difficult diseases to diagnose because the emboli can be small. The emboli are transparent to conventional X-rays and produce only non-specific symptoms.

In the current technology, diagnosis of pulmonary embolism is generally performed by a pulmonary anteriogram, a technique where a catheter is placed through the heart into the pulmonary artery. An X-ray opaque liquid dye (X-ray dye) is injected through the catheter into the lungs, after which an X-ray movie (angiogram)is used to visualize blood flow through the lungs.

There is also a non-invasive method to diagnose pulmonary embolism which utilizes biodegradable albumin aggregates labeled with radioactive technetium 99 m. The technique involves injection of the aggregates into a vein allowing the aggregates to lodge in the lungs. Visualization of the aggregates is performed by a nuclear camera which detects the radioactive emission or so-called "radio-label".

The current technology for diagnosing pulmonary embolism is inadequate due to the fact that patients are hesitant to have this procedure performed routinely. Further, the insertion of a catheter into the heart and lungs is a surgical procedure, limiting use of this method to hospitals and requiring complex equipment to produce acceptable sequential images.

Use of radioactively labeled biodegradable albumin aggregates has several disadvantages. First, the method is very expensive to use because it is radioactively based. Reasons for these high costs include expensive radioactive measuring equipment and the necessity of protecting medical personnel from radiation exposure. Secondly, the radioactively labeled aggregates have a limited shelf-life, ranging from one week to several months. Even where the shelf-life is at the high end of this range, the continuous decay makes frequent recalibration of the testing apparatus necessary. Finally, this type of test is also limited to hospitals because of the expense of obtaining the proper equipment. Aside from the materials, the costs involved in minimizing radiation exposure for these individuals is substantial. Patients are also hesitant to undergo testing involving the insertion of radioactive materials into their bodies. All of these problems result in low usage of this type of test.

In addition to the disadvantages described above, the non-invasive radioactive tests have poor reliability because the resolution of the images is limited and small emboli cannot be detected. The patients must be flat for many minutes to allow sufficient radioactive disintegration to occur in order to provide enough information to create the image. Otherwise, small movement blurs the image thereby limiting image isolation.

Because of the problems and disadvantages associated with current methods of diagnosing pulmonary embolism, there is substantial under-utilization of pulmonary embolism testing in relation to the frequency of occurrence of the disease. What is needed, therefore, is a method of diagnosing pulmonary embolism that is accurate, inexpensive to use, inoffensive to patients and capable of being used in a traditional doctor's office. The present invention satisfies these needs and provides other related advantages.

OBJECTS OF THE INVENTION

It is, therefore, one of the primary objects of the present invention to provide a method of visualizing a bloodstream circulation in an animal body by utilizing microspheres having an imaging energy contrast material thereon or therein.

It is another object of the present invention to provide a method of the type stated for visualizing an arterial circulation by allowing the microspheres to be carried in a subject's circulatory system and subjecting the microspheres to an imaging energy.

It is a further object of the present invention to provide a method of the type stated which utilizes microspheres bearing an X-ray absorbent material such that the microspheres will absorb the X-rays thereby enabling the visualization of the position of the microspheres in a circulatory system.

It is also an abject of the present invention to provide a method of the type stated in which microspheres may be properly labeled and subjected to imaging energy of different types for precisely locating and visualizing a bloodstream circulation by examining a contrast between the microspheres and body tissue around the subject's circulatory system.

It is an additional object of the present invention to provide a unique method of enabling the diagnosis of a pulmonary embolism using contrast labeled microspheres carried in the circulatory system of a subject.

It is still another object of the present invention to provide a method for preparing X-ray opaque microspheres on a relatively simple and economical basis.

It is still a further object of the present invention to provide microspheres comprised of a biodegradable substance and an imaging energy material in an amount sufficient to absorb imaging energy.

With the above and other objects in view, our invention resides in the novel steps of the method and the features and ingredients of the composition as hereinafter described and pointed out in more detail.

BRIEF SUMMARY OF THE DISCLOSURE

The present invention resides in the use of biodegradable microspheres which are labeled with an imaging energy contrast material and which is typically an imaging energy "opaque" material which can be used to visualize an arterial circulation. In this way, it is possible to enable the diagnosis of a pulmonary embolism and other maladies. The present invention also resides in a method of preparing the microspheres.

Diagnosis of pulmonary embolism using the present invention is accurate and easy to perform, allowing testing to be conducted in a doctor's office. The present method is also relatively inexpensive and poses no health problems for medical personnel since there is an absence of radioactivity.

The present invention involves the labeling of biodegradable microspheres with an imaging energy contrast material, as aforesaid, that is, the application of a contrast material to the microspheres. The contrast material may adopt may forms, as hereinafter described, although the contrast material may be applied to the surface of the microspheres, or the microspheres, which are typically solid, as opposed to hollow spheres, can be pregnated with the contrast material.

In one form, the contrast material may adopt the form of a simple dye which is either applied to the surfaces of the microspheres, or otherwise pregnated into the body of the microspheres. However, other types of contrast materials, as for example, the contrast materials used in conventional angiography procedures may be employed.

One of the preferred forms of imaging energy which may be used in accordance with the present invention is X-ray energy. In this way, when the microspheres are labeled with a X-ray absorbent material, the microspheres will become X-ray absorbent or so-called "X-ray opaque" when subjected to X-ray energy. However, other forms of imaging energy, as for example, ultrasound utilizing ultrasonic energy, nuclear magnetic resonance and the like may be employed in accordance with the present invention. The exact form of imaging energy is not critical with respect to the invention. It is only important to have the contrast labeled microspheres capable of being rendered imaging energy absorbent with respect to the surrounding tissue in a subject's body. However, the use of X-ray absorbent materials and X-rays as the imaging energy source is preferred in accordance with the present invention and the present invention is specifically described in terms of the use of X-ray absorbent materials with X-ray energy.

The method of the present invention, in a preferred embodiment, involves labeling biodegradable microspheres with X-ray absorbent material, making the microspheres themselves X-ray absorbent or so-called "X-ray opaque". An "X-ray absorbent" substance will absorb X-rays, and will therefore appear as a white area on a developed X-ray film; whereas a tissue or area which transmits X-rays will appear dark on the X-ray film.

The X-ray opaque microspheres are injected into a peripheral vein and are carried to the lungs, where they become lodged in small blood vessels. If a blood clot is present in the lungs, the microspheres will not be carried to blood vessels that are downstream of the blood clot. The lungs are then X-rayed and the resulting X-ray image is examined. The majority of blood vessels in the lungs will show as white areas in the X-ray because of the presence of the X-ray absorbent microspheres lodged in the small capillaries. The blood clot and any area of the lungs to which blood flow is restricted, whereby being devoid of X-ray laden microspheres, however, will show as dark areas on the X-ray, since these areas of the lungs will have transmitted the X-rays.

The microspheres are composed of a biodegradable material that dissolves into the blood within fifteen to thirty minutes after their introduction. The dissolved microspheres are degraded in the body and the X-ray dye excreted out of the body usually via the urine.

The microspheres used with the present invention are biodegradable and are designed to dissolve into the bloodstream within fifteen to thirty minutes after their introduction. They may be of various compositions, including albumin, and starch, with albumin being preferred. The term "microsphere" is used to represent generally spherically shaped particles with each particle ranging in size from about 9 u to about 100 u and preferably from about 10 u to about 50 u. A "uniform" size grouping of microspheres used with the present invention may preferably contain microspheres ranging in size anywhere from 10 u to 50 u in diameter.

Albumin microspheres used with the present invention are prepared by injecting droplets of an albumin solution into rapidly stirred oil. The microspheres are stablized either by heating or by cross-linking with glutaraldehyde, and are washed with ethyl ether or petroleum ether and then dried by a suitable drying agent or drying mechanism. The ultimate size of the microspheres is controlled by the speed with which the oil is stirred, the size of the albumin droplets, and by whether the albumin solution is pre-dispersed in oil by sonication.

X-ray absorbent material is mixed into the initial solution before droplet injection so as to make the microspheres themselves X-ray absorbent. Various materials may be used for this purpose, including potassium iodide (KI) and hypaque-sodium, the latter being preferred. Hypaque-sodium is a soluble solid having four-iodine atoms per molecule, making it ideal for use with the microspheres of the present invention.

The X-ray absorbent microspheres are injected into a peripheral vein and allowed a short time to circulate through the lungs. A chest X-ray is taken and examined. The presence of the X-ray absorbent microspheres allows visualization of the arterial circulation within the lungs, as blood vessels in the lungs containing the microspheres will show up as white areas on the X-rays, in contrast to the surrounding tissue structure. If a blood clot is present, the clot will transmit the X-rays and will therefore show as a dark area, in contrast to the other blood vessels in the lungs. Similarly, any area of the lungs to which blood flow has been restricted as a result of the blood clot will also show as dark areas in contrast to the other blood vessels in the lungs containing X-ray absorbent microspheres.

The microspheres used with the present invention are composed of albumin or other biodegradable materials so there will be no residue or lasting physiological effects to the body once the test is concluded. The microspheres are designed to dissolve into the bloodstream within fifteen to thirty minutes after introduction into the body, the exact time period being a function of their composition and size. This time period is sufficient to conduct the test of the present invention, but not too long so as to cause any damage to the lungs. After dissolution, the X-ray dye is passed out of the body in the urine and the albumin is degraded by the liver.

The arterial circulation visualization method of the present invention, which enables diagnosis of pulmonary embolism, provides dynamic advantages over the X-ray movie and radioactive methods used currently. As compared to radioactive albumin aggregates, costs with the present invention are significantly decreased due to the lack of necessity for radiation detection and protective equipment. The present method is much safer because there is no exposure of the patient and medical personnel to harmful radioactivity, and is also much more reliable than radioactively based methods. As compared to invasive techniques, such as an injection of X-ray absorbent dye and visualization using an X-ray movie, the present method is much less offensive to patients and is simplier to perform. Unlike both radioactively based and X-ray dye injection methods, the method of the present invention may be used to diagnose pulmonary embolism in a doctor's office.

This invention possesses many other advantages and has other purposes which may be made more clearly apparent from a consideration of the forms in which it may be embodied. These forms have been described generally in this brief summary forming part of the present specification. They will now be described in more detail for purposes of illustrating the general principles of the invention, but it is to be understood that such detailed description is not to be taken in a limiting sense.

DETAILED DESCRIPTION OF THE PREFERRED EMBODIMENT

The present invention is embodied in the use of biodegradable microspheres labeled with imaging energy absorbent material to visualize an arterial circulation, thereby enabling the diagnosis of pulmonary embolism. The present invention also involves the method of preparing such microspheres which are labeled with the contrast material.

The present invention is described generally with respect to X-ray absorbent contrast materials and the use of X-ray energy as the imaging energy. However, this is only for purposes of illustrating the principle embodiment of the invention and it is to be understood that the invention is not so limited. Some of the other types of imaging energy which may be used include for example, ultrasound which is qenerally a microwave type of radiation. The microspheres are generally more echo dense than is the surrounding tissue in an animal body. Thus, if the microspheres are allowed to flow in a blood circulation as for example, an arterial circulation, the microspheres will become lodged in capillaries of the tissue. The use of the ultrasound energy will immediately enable a contrast between the surrounding tissue and the microspheres which become lodged in the capillaries of that tissue.

Another form of imaging energy which may be used in accordance with the present invention is computer axial tomography also referred to as "cat scanning". Here again, the microspheres have a much greater density than the blood or the surrounding tissue and the cat scanning allows for imaging of the microspheres with respect to the blood and surrounding tissue.

A further form of imaging energy which may be used in accordance with the present invention is nuclear magnetic resonance. This form of imaging energy will show the blood flow as in a hollow tube. The contrast in the spheres will allow the spheres to be imaged with respect to the surrounding tissue and in the depicted hollow tube.

The present invention is effective in visualizing a blood stream circulation, such as an arterial circulation. However, the invention is also effective in visualizing a venal circulation, as well as circulation in the capillaries. Generally, the labeled biodegradable microspheres are used in visualizing an arterial circulation in order to diagnose a pulmonary embolism. Thus, the microspheres are injected into an artery and allowed to flow into the capillaries where they will become lodged. At this point, the biodegradable microspheres are effective for purposes of absorbing imaging energy and thereby contrasting the surrounding blood and tissue.

In a more preferred embodiment, the method of the present invention involves dyeing microspheres, composed of albumin or other materials, with an X-ray absorbent material so as to make the microspheres themselves X-ray absorbent. These X-ray absorbent or opaque microspheres are then injected into the bloodstream of a patient and are distributed to the arterial circulation area to be visualized. An X-ray of the area is taken and developed. If the arterial circulation area is the lungs, for example, blood vessels in the lungs filled with X-ray absorbent microspheres will show as white areas on the X-ray, while a blood clot and blood vessels of the lungs to which blood flow has been restricted will have transmitted the X-rays and consequently will show as dark areas. Within fifteen to thirty minutes after injection of the X-ray absorbent microspheres into the bloodstream, they are dissolved and subsequently excreted from the body, via the urine, leaving no lasting physiological effects.

When used to diagnose pulmonary embolism, the method of the present invention provides significant advantages over the use of X-ray dye and radioactively treated biodegradable aggregates, which are currently the most common methods used for such diagnosis. The present method poses no health hazards to medical personnel and patients and costs significantly less to use because there is no need to protect medical personnel from radioactivity, or to purchase radioactivity measuring equipment. The present method is also less complex then current methods in that simple X-rays are used to conduct the test and there is no insertion of foreign materials into the heart and lungs. This allows the method of the present invention to be used to diagnose pulmonary embolism in a doctor's office. Further, the present method is much more reliable then a radioactively based method.

The term "microsphere" is used to represent a particle ranging in size from about 9 u to about 100 u and preferably about 10 u to about 50 u in diameter, as previously stated. A particular group of "uniformly" sized microspheres may include particles having a diameter anywhere in this range.

The microspheres of the present invention may be composed of any biodegradable material that is capable of being formed into microspheres in the desired size range. Possible biodegradable materials include, but are not limited to, human albumin, and starch, with human albumin being preferred.

The starches which may be used to form the microspheres of the present invention are usually polysacharides which are biodegradable by blood stream enzymes. Other materials which may be used to form the microspheres are certain fats, such as lipid particles, triglycerides, lyphoproteins and free fatty acid lipids, as well as mixtures of the foregoing.

Any type of contrast material which is used for example, in angiography may be used in the present invention. Some of the X-ray absorbent materials which are used as contrast materials are hereinafter described in more detail. Nevertheless, other contrast agents which may be pregnated throughout the microspheres include sodium diatrizoate, sodium meglumine and related organic iodides. Additional contrast materials which may be included are hereinafter described in more detail. Any of these materials may be used generally with any of the forms of imaging energy described above.

As shown in Example 1, X-ray absorbent albumin or other microspheres may be prepared by injecting droplets of a congealing solution containing albumin and hypaque-sodium into cotton seed oil that is being rapidly stirred. The congealing solution is one which causes the albumin or other biodegradable material to congeal upon contact.

The temperature of the congealing bath is usually maintained within the range of about 90 degrees C to about 120 degrees C. However, the bath could be maintained at a temperature as low as about 75 degrees C and as hiqh as about 200 degrees C. and temperatures within this range constitute a congealing temperature. While at this temperature, and with rapid stirring, the microsphere forming material is introduced into the bath.

A large number of oils may be used in place of cotton seed oil and include, for example, linseed oil, maleic acid, etc. In effect, the congealing solution can be any lipid liquid form. A congealing solution enables formation of the droplets, inasmuch as the protein materials which are introduced into the lipid congealing solution are entirely immiscible and thereby cause the protein biodegradable materials to form into the small microspheres.

The contrast material is mixed with the albumen or other starch which may be used to form the microspheres, prior to introduction into the oil bath. In this way, the contrast material may be completely intersperced or pregnated, that is laced throughout the body of the generally solid microsphere as it is formed. However, it should be understood that the contrast material could be applied to the surfaces of the microspheres after the latter have been formed.

After the formation of the microspheres in the bath, the oil is drained and the microspheres are allowed to dry. Usually, the microspheres can be introduced into ether or acetone for effective drying and removal of any surface oil remnants. However, this form of drying only constitutes a surface drying. Nevertheless, at this point in the process the spheres are discrete microspheres. They may then be weighed in order to determine the size of the microspheres in order to determine the number of microspheres which may be injected into a subject.

The microspheres may also be washed with alcohols, and preferably lower molecular weight alcohols. Thus, 95% ethanol, denatured isopropyl alcohol, etc. may be used. Highly effective washing solutions have been found to be certain ethers, such as ethyl ether or petroleum ether. The microspheres are stablized either by heating, as shown in Example 1, or by cross-linking as for example with glutaraldehyde. The microspheres are then dried, by any rapidly evaporating alcohol, as for example, ethyl ether as mentioned above. The stablized microspheres may also be dried by heating in air or drying in a vacuum. When utilizing air or vacuum drying, the microspheres are heated for a suitable drying time, about 10 to about 30 minutes, preferably at a drying temperature of about 50 degrees F to about 150 degrees F.

In preparing the microspheres, usually about 2 parts of albumin or other starch is used with about one part of contrast material. Moreover, the amount of oil which is used, by weight, should be at least 20 to 50 times greater than the total weight of the contrast material and the starch which is introduced into the oil bath. The contrast material is usually used in an amount of about one part of contrast material to about ten parts of starch. However, the amount of contrast material used with respect to the amount of starch can vary widely, as for example, ten parts of contrast material could be used with one part of starch. The greater the amount of contrast material, the greater the imaging energy absorbent capabilities of the microspheres will be.

The size of the microspheres are determined to some extent by the washing and drying steps. Preferably they should be about 2 to about 100 microns in size. The washing in the various alcohols should take place no longer than about 10 minutes. Moreover, drying should take place for about 10 to about 30 minutes, as aforesaid, and preferably about 25 minutes to about 60 minutes at a temperature within the range of about 50 degrees F to about 150 degrees F.

The dried albumin microspheres have the X-ray absorbent hypaque-sodium incorporated into them, making them X-ray absorbent. Bones and tissues within the human body absorb X-rays, which allows them to be viewed using conventional X-ray techniques. A substance that is "X-ray absorbent" or "X-ray opaque" also absorbs X-rays and is therefore visible using X-ray techniques. Therefore, X-ray absorbent materials show as white areas on a developed X-ray film. Thus, for example, the normal human lung will appear dark in an X-ray film. However, when the X-ray absorbed microspheres appear in the lung capillaries, those regions will appear white on an X-ray film due to the fact that they absorb the X-rays. If an embolism is present, the regions downstream of the embolism which do not receive the X-ray absorbed microspheres will thereby also appear to be dark on an X-ray film.

Potassium iodide (KI) may also be used to render the albumin microspheres X-ray opaque. The resulting albumin microspheres have KI crystals on their surfaces and partially incorporated into their structure.

Ions other than potassium iodide can also be used. For example, iron is also an effective X-ray absorbent material. In accordance with the present invention, it has been found to be highly effective to use a combination of both potassium iodide and iron. In this way, using multiple ions, it is possible to reduce the concentration of X-rays to a point where they will be non-toxic, but yet will still be sufficient to make the microspheres X-ray absorbent.

One of the known contrast agents which is usually employed is the sodium hypaque, often known as "Hypaque". The sodium hypaque is often known as "diatrizoate" and is chemically sodium 3, 5, diacetamido 2, 4, 6 triiodobenzoate. This composition generally contains at least 50 percent and usually 59.87 percent of iodine.

The sodium hypaque is usually available in a powder form and in a liquid form. The powder provides about 600 milligrams of organically bound iodine per gram of powder and contains a caramel coloring agent. The liquid solution is also available and usually contains about 41.66 percent of iodine. Each cc generally contains about 249 milligrams of organically bound iodine. If the diatrizoate is in a liquid form, it is simply dehydrated back into a crystalline form and then reconstituted, as for example, with a 5 cc saline solution for combining with the human albumen to make contrast microspheres.

Other contrast agents which are currently used in, for example, angiography, and which can be used in accordance with the present invention include metrizamide, often known as "Amipaque" and which is offered by the Winthrop Corporation. Metrizamide is a non-ionic water soluable contrast medium. Another contrast agent which can be employed is iopanoic acid and which is an iodine radio opaque medium, often known as "Telepaque". Ioglaxate, often known as "hexabrix" is another suitable contrast agent. Ioglaxate is a non-ionic non-hyperamore contrast agent offered by the Mellencoft Company. A further contrast agent which may be employed is meglumine offered by the Squibb Pharmaceutical Company and is an organic iodine X-ray opaque medium.

Most of the contrast agents which may be used contain an organic iodine molecule which is the energy absorbent portion capable of absorbing the X-rays. As a result, the X-rays do not penetrate the molecules and show up as a defect on the X-ray.

Diagnosis of pulmonary embolism, as shown in Example 2, first involves injecting X-ray opaque microspheres, such as those prepared in Example 1, into a peripheral vein. The microspheres travel to the lungs where they become lodged in the blood vessels. If a blood clot is present in the lungs, no microspheres will flow to areas of the lungs that are directly downstream of the clot.

Within fifteen minutes of injection of the X-ray opaque microspheres, a chest X-ray of the patient is taken and developed. Areas of the lungs containing the X-ray opaque microspheres will show on the developed X-ray as white areas, as the microspheres in those blood vessels will absorb the X-rays. Areas of the lungs to which blood flow has been restricted by the blood clot will show as dark areas on the developed X-ray because they will have transmitted the X-rays. The blood clot itself, of course, will also show as a dark area.

Even if there is no blood clot present in the lungs, the method of the present invention enables visualization of the arterial circulation of the lungs. Arterial circulations in other parts of the body can also be viewed by varying the point of injection into the bloodstream proximal to the organ.

The microspheres can be injected into the body at any desired location in order to enable X-ray inspection of the desired regions of the body. For example, when using the method of the present invention to determine the presence of a blood clot in the lungs, the microspheres are introduced into a vein for return to the heart. These microspheres will pass through the heart and move directly into the lungs. In this way, the microspheres, which are slightly larger than red blood cells, will be captured in the small capillaries of the lungs.

If it is desired to X-ray analyze a hand or other portion of the body, the microspheres would be injected into an artery upstream of the organ or other body tissue which is to be examined.

Within fifteen to thirty minutes after introduction into the bloodstream, the microspheres of the present invention are totally biodegraded by the blood and become dissolved therein. The exact dissolution time is a function of the composition and size of the microspheres. This time period is sufficiently short that no physiological damage to the patient results. The dissolved microspheres are ultimately passed out of the body in solution via the urine.

The following examples will serve to illustrate the present invention in accordance with preferred embodiments.

EXAMPLE 1

Preparation Of X-Ray Opaque Microspheres Using Albumin and Hypaque-Sodium

Human albumin (110 mg) was dissolved in 3 ml of distilled water, to which hypaque-sodium (500 mg/100 gm albumin) was added. Cotton seed oil (100 ml) was heated to 40 degrees C in a 150 ml beaker on a hot plate with high-speed mechanical stirring using a polyethylene three-blade propeller with an Eberbach Con-Torque stirring motor. The albumin-hypaque-sodium solution was injected into the oil by drop-wise addition from a syringe with a 25 gauge needle, the oil being stirred and heated continuously during this addition. The addition of the albumin-hypaque-sodium solution raised the temperature of the oil about 20 degrees C. Stirring and heating were continued until the oil reached 115 degrees C, in approximately fifteen minutes. The temperature was maintained at 115 degrees C for ten minutes.

During the addition of the albumin-hypaque-sodium solution, the stirred emulsion first became very turbid and then cleared as the albumin droplets dehydrated. The preparation felt gritty when a drop was rubbed between fingers.

After cooling of the emulsion, the microspheres settled rapidly and most of the supernatant oil was decanted. The remainder of the suspension was centrifuged and the oil aspirated. The microspheres were washed four times with ethyl ether and air dried in a fume hood.

Alternative materials and techniques are available at various stages of the above process. For example, potassium iodide (KI) substituted for hypaque-sodium at the same concentration yielded a product in which KI crystals were present on the surface of the microspheres and were partially incorporated into the interior of the microspheres. Stabilization of the microspheres, accomplished by heating in the above-described process, may also be accomplished by cross-linking the microspheres with glutaraldehyde. The microspheres may be washed with petroleum ether instead of ethyl ether.

EXAMPLE II

The arterial circulation of a dog was visualized by injecting 5 mg of X-ray labeled microspheres (100 micron size) into the superior vena cava. During and following the injection, the X-ray images of the dogs right heart, pulmonary arteries, and lungs were recorded on video tape. The X-ray images were produced using standard fluoroscopy equipment interfaced with a television camera and video recorder.

Following the injection, the right atrium, right ventricle and pulmonary artery became radio-opaque as the microspheres passed through those structures. The microspheres then lodged in the pulmonary arterioles of approximate 100 u size. Thus, a random sample of the entire distribution of 100 u arterioles became visualized as the microspheres lodged in those arterioles. The course of the arteries, which were previously radio-translucent, could be visualized when rendered radio-opaque by the microspheres. The arterioles remained visable for about 30 minutes and became radio-translucent as the microspheres dissolved. A single X-ray film at 10 minutes after injection would visualize the pulmonary circulation. A pulmonary embolism would be visualized as a defect in the expected distribution of blood vessels; e.g. you could see a dark area where the remaining lung marked with radio-opaque microspheres would be white as seen in the fluoroscopic images.

EXAMPLE III

Approximately 500,000 microspheres having about 20 to about 50 nanograms of contrast material was reconstituted with 3 cc of saline solution. This mixture was then further mixed with 7 cc of sheep blood for a total period of about 3 minutes. Mixing occurred vigorously in a glass beaker.

A sheep having a weight of about 40 kilograms was anesthetized with chloralose. A catheter was introduced into the right mid-pulmonary artery of the sheep under fluoroscopic control. The mixture was thereafter introduced through the catheter into the mid-pulmonary artery.

A fluoroscopic video system recorded from time zero to the first 30 seconds and showed a definite blush of the contrast microspheres being selectively trapped in the arterials and the capillaries of the lung segment. The X-ray opaque spheres were illustrated as a dark spot on the X-ray film.

In addition, plain chest X-rays were also taken at time zero, one minute, five minutes, ten minutes, 30 minutes, one hour, 1½ hours and two hours after the beginning of the test. The contrast spheres were vividly outlined against the background of the tissue in the lung which did not contain any of the contrast spheres. Electrocardiograph measurements were made and arterial blood gas measurements were made. There were no electrocardiograph changes or arterial blood gas changes with the injection. The pulmonary artery pressures also remained normal.

At the conclusion of the experiment, the animal was sacrificed and the right lung was removed. Plain X-rays of the lung were then taken. The X-ray film clearly showed the region with the microspheres being X-ray opaque and being vividly separated from the tissue not containing the microspheres. The lung was then taken to a pathology laboratory for sectioning and H and E stained for evidence of inflammation.

Prior to sacrificing of the sheep, a gelfoam clot was injected selectively into the left middle pulmonary artery thereby inducing a blood clot and pulmonary embolism. As anticipated, standard X-ray indicated no change.

The catheter was then pulled back into the vena cava and approximately 500,000 of 20–50 micron contrast spheres were injected into the vena cava after a dilation. The contrast spheres were then imaged continually on fluoroscopic videotape. Further, chest X-rays were taken at time zero, one minute, five minutes, 15 minutes, 30 minutes, one hour, 1½ hours and two hours from the time of the injection. The fluoroscopic videotape as well as the X-rays showed all portions of the pulmonary artery and the capillary circulation.

EXAMPLE IV 1,000,000 microspheres were reconstituted with 3 cc of a normal saline solution. This mixture was then mixed with 7 cc of dog blood from a 20 kilogram mongrel dog. The dog was anesthetized with chloralose and a Harvard respirator was used. A catheter was inserted into the main pulmonary artery and the microspheres in the saline solution and dog blood solution mixture were introduced into the pulmonary artery. The microspheres were in about the 50–80 micron size range.

Digital subtraction angiography was then taken at 7 frames per second over the first minute and this was followed by Franklin cut films at time zero, five minutes, 15 minutes, 30 minutes, one hour, two hours, three hours and four hours. An outline of the arterial tree, which manifested as dark spots on the X-ray film was easily discernible on the film. The films were placed on a computer tape and the Franklin cut films were developed with Scout films for comparison. The arterial tree of the pulmonary circulation with the 50–80 micron spheres was easily observed. Dense X-ray opacity was also noticed for up to about 1½ hours and then the X-ray films returned to a normal condition within about 4 hours at which time the microspheres had completely biodegraded.

Thereafter, a catheter was selectively introduced into the left lower pulmonary artery. Two large clumps of gel-foam were then injected into this lowerer pulmonary artery inducing a pulmonary embolism. This was followed by a pulmonary angiograph on digital and Franklin cut films. The angiograph clearly outlined the occluded main pulmonary arteries going to the segments of the lower and mid-left lung.

The catheter was then pulled back and an additional 500,000 of the 50–80 micron contrast spheres were again injected and a clearly defined pie-shaped defect was observed on both the standard X-ray films and on the digital subtraction X-ray plain films. This was due to the fact that with the occlusion of the vessel, the contrast spheres did not enter the capillaries or the arterials and thus showed less penetration of the X-ray film and hence a light spot on the film.

30 minutes after the gel-foam injection, clot formation developed resulting in a pulmonary infarction and then additional contrast microspheres were injected. The animal was sacrificed and the right and left lungs were taken to a pathology laboratory for H and E photomicrographs. These micrographs showed the microspheres and the arterials degrading by giving up the contrast crystals from the surfaces of the albumin spheres. There was no evidence of inflammation induced by these spheres at the capillary and arterial level for up to 4 hours.

EXAMPLE V

20–40 micron contrast spheres in an amount of about 500,000 were mixed with 3 cc of a saline solution and then further mixed with 7 cc of the blood of a 25 kilogram mongrel dog. A catheter was introduced into the left coronary under fluoroscopic control and liquid contrast was used to document the anatomy. The 20–40 micron contrast spheres in solution were injected into the left coronary and digital subtraction angiography and plain X-rays were obtained at 30 seconds, one minute, five minutes and 10 minutes thereafter. The angiography and X-rays clearly depicted the coronary artery.

Digital and standard X-ray films were then taken of the arterial phase and the capillary phase.

The animal was then sacrificed and these sections were fixed with formalin and with an H and E stain.

Prior to the coronary study in this 25 kilogram dog, a catheter was selectively placed into the mesentery artery of the gut. 500,000 of the same type of spheres was then injected. Digital and plain X-ray films were taken at time zero and outlined the mesentery artery.

Thereafter, the catheter was selectively placed in the upper pole of the right kidney and a gel foam clot was introduced into the right kidney thereby occluding the upper renal artery. After about 30 minutes, and in the right main renal artery, 500,000 microspheres were injected. X-ray pictures with digital and cut films were taken at time zero, and at 5 minutes, 15 minutes, 30 minutes and one hour thereafter showing the defect of the upper pole and the remaining kidney.

Thus there has been described a unique and novel method of enabling visualization of a bloodstream circulation as well as a method of diagnosing pulmonary embolism and a method of preparing biodegradable X-ray opaque microspheres which fulfills all of the objects and other advantages which have been sought. It should be understood that many changes, modifications, variations, and other uses and applications of the described methods and the articles will become apparent to those skilled in the art after considering this specification. Therefore, any and all such changes, modifications, variations and other uses and applications are deemed to be covered by the spirt and scope of this invention.

Having thus described our invention, what we desire to claim and secure by letters patent is:

1. A non-toxic method of visualizing circulation in the bloodstream of a subject comprising the steps of:
   a) selecting a quantity of contrast agent laden microspheres which will enable generation of an image and for a desired duration when injected into the bloodstream of a subject and which microspheres are laden with a non-toxic amount of a non-metallic imaging energy responsive material but which is nevertheless sufficient to enable imaging when subjected to an imaging energy;
   b) injecting the selected quantity of non-metallic biodegradable imaging energy responsive microspheres into the bloodstream of the subject at a point in the subject's circulatory system such that said microspheres are carried to a bloodstream circulation area sought to be visualized, said microspheres being sold and having the contrast agent inculcated throughout the microspheres, said microspheres also having a size with respect to the bloodstream circulatory system which is to be imaged such that the microspheres will lodge within the bloodstream circulatory system, and said microspheres further being sufficiently cross-linked so that they will not readily dissolve in the bloodstream in a short time and which will thereby remain in that circulatory system for a time sufficient to be subjected to imaging;
   c) subjecting said bloodstream circulation area to electromagnetic wavelength imaging energy of a type which is absorbed by said microspheres to form an image of said bloodstream circulation area without resulting in toxicity to the subject; and
   d) examining said image for the presence of said microspheres, which will enable visualization of said circulation area by response of said microspheres to the imaging energy, and thereafter enabling said microspheres to be absorbed in the bloodstream without resulting in toxicity to the subject.

2. A method as set forth in claim 1 wherein said imaging energy responsive material is absorptive of the imaging energy.

3. A method as set forth in claim 1 wherein said bloodstream circulation is an arterial circulation.

4. A method as set forth in claim 1 wherein said microspheres are comprised of human albumin.

5. A method as set forth in claim 1 wherein said microspheres are X-ray absorbent by virtue of their being laden with an X-ray opaque material.

6. A method as set forth in claim 1 wherein said microspheres are X-ray absorbent by virtue of their being laden with potassium iodide.

7. A method as set forth in claim 1 wherein said microspheres are X-ray absorbent by virtue of being laden with hypaque-sodium.

8. A method as set forth in claim 1 wherein said microspheres have a size on the order of about 9 u to about 100 u in diameter and are thereby sized to become lodged in capillaries and arteries of the bloodstream circulatory system.

9. A method as set forth in claim 1 wherein said microspheres have a size on the order of about 10 u to about 50 u in diameter and are thereby sized to become lodged in capillaries and arteries of the bloodstream circulatory system.

10. A method as set forth in claim 1 wherein said arterial circulation is a pulmonary circulation.

11. A method as set forth in claim 1 wherein said biodegradable microspheres are dissolved in said bloodstream within about 15 to about 30 minutes after introduction into said bloodstream and which time is sufficient to obtain an imaging of a portion of the bloodstream circulatory system.

12. A non-toxic method of diagnosing pulmonary embolism in the bloodstream of a subject comprising the steps of:
   a) selecting a quantity of non-metallic microspheres and which are laden with a non-toxic amount of a non-metallic imaging energy absorbent material but with an amount which is nevertheless sufficient to enable imaging when subjected to imaging energy, and which will thereby enable generation of an image and for a desired duration when injected into the bloodstream of a subject;
   b) injecting the imaging energy absorbent non-metallic microspheres into the bloodstream of said subject at a point in the circulatory system such that said microspheres will be carried to the pulmonary circulation, and having the imaging energy material inculcated throughout the microspheres, said microspheres also having a size with respect to the pulmonary circulation such that the microspheres will become lodged in the pulmonary circulation, and said microspheres further being sufficiently cross-linked so that they will not readily dissolve in the bloodstream in a short time and which will thereby remain in the pulmonary circulation of the subject for a time sufficient to be subjected to imaging;
   c) subjecting said pulmonary circulation to imaging energy of a type which is absorbed by said microspheres to form an image of said pulmonary circulation without resulting in toxicity to the subject;

d) conducting an examination of said image for the presence of said microspheres and thereafter enabling said microspheres to be absorbed in the bloodstream of the subject; without resulting in toxicity to the subject and e) determining from said examination whether a pulmonary embolism is present.

13. A method as set forth in claim 12 wherein said pulmonary circulation is a pulmonary arterial circulation.

14. A method as set forth in claim 13 wherein said imaging energy is X-ray energy.

15. A method as set forth in claim 14 wherein said microspheres are comprised of human albumin.

16. A method as set forth in claim 15 wherein said microspheres are X-ray opaque by virtue of their being laden with hypaque-sodium.

17. A method as set forth in claim 15 wherein said microspheres are X-ray opaque by virtue of their being dyed with potassium iodide.

18. A method as set forth in claim 13 wherein said microspheres have a size on the order of about 9 u to about 100 u in diameter and are thereby sized to become lodged in arteries and capillaries of the pulmonary circulation.

19. A method as set forth in claim 13 wherein said microspheres have a size on the order of about 10 u to about 50 u in diameter and are thereby sized to become lodged in arteries and capillaries of the pulmonary circulation.

20. A method as set forth in claim 13 wherein said biodegradable microspheres dissolve in said bloodstream within about 15 minutes to about 30 minutes after introduction into said bloodstream and which time is sufficient to obtain an imaging of a portion of the pulmonary circulation.

21. A non-toxic method of visualizing an arterial circulation in the bloodstream of a subject comprising the steps of:

a) selecting a quantity of non-metallic microspheres and which are laden with a non-toxic amount of non-metallic X-ray absorbent material but with an amount which is nevertheless sufficient to enable imaging when subjected to X-ray energy, and which will enable generation of an X-ray image and for a desired duration when injected into the bloodstream of a subject;

b) injecting biodegradable X-ray absorbent microspheres into the bloodstream of the subject at a point in the subject's circulatory system such that said microspheres are carried in the bloodstream to a bloodstream circulation area sought to be visualized, said microspheres being solid and having the X-ray absorbent material inculcated throughout the microspheres, said microspheres also having a size with respect to the bloodstream circulatory system which is to be visualized such that the microspheres will lodge within the bloodstream circulatory system, and said microspheres further being sufficiently cross-linked so that they will not readily dissolve in the bloodstream in a short time and which will thereby remain in the circulatory system for a time sufficient to be subjected to X-ray imaging;

c) subjecting said circulation area to X-rays to form an X-ray image of said circulation area ans causing the microspheres to absorb the X-rays to render them X-ray opaque for contrast against surrounding or adjacent tissue without resulting in toxicity to the subject;

d) examining said X-ray image for the presence of white areas on an X-ray film to represent the presence of said microspheres, which will enable visualization of said circulation by means of the absorption of X-rays by said microspheres; and e) thereafter permitting the microspheres to become degraded in the body after a period of time for visualization which is sufficient to enable X-ray imaging but which is not sufficiently long to create damage to the tissue in which the visualization of the circulation is taking place and which will not result in toxicity to the individual.

* * * * *